United States Patent
Glielmi et al.

(10) Patent No.: US 9,400,317 B2
(45) Date of Patent: Jul. 26, 2016

(54) MR SCAN SELECTION FOR PET ATTENUATION CORRECTION

(71) Applicants: Christopher Glielmi, Hoboken, NJ (US); Christian Geppert, Hoboken, NJ (US); David Faul, Brooklyn, NY (US); Matthias Fenchel, Erlangen (DE)

(72) Inventors: Christopher Glielmi, Hoboken, NJ (US); Christian Geppert, Hoboken, NJ (US); David Faul, Brooklyn, NY (US); Matthias Fenchel, Erlangen (DE)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 317 days.

(21) Appl. No.: 14/091,372

(22) Filed: Nov. 27, 2013

(65) Prior Publication Data
US 2014/0153806 A1   Jun. 5, 2014

Related U.S. Application Data

(60) Provisional application No. 61/733,132, filed on Dec. 4, 2012.

(51) Int. Cl.
*G01R 33/48* (2006.01)
*A61B 5/055* (2006.01)
*A61B 6/03* (2006.01)
*A61B 5/00* (2006.01)
(Continued)

(52) U.S. Cl.
CPC ............ *G01R 33/481* (2013.01); *A61B 5/0037* (2013.01); *A61B 5/055* (2013.01); *A61B 6/037* (2013.01); *A61B 6/4417* (2013.01); *A61B 6/5247* (2013.01); *A61B 6/5258* (2013.01); *G06T 5/008* (2013.01); *G06T 5/50* (2013.01); *A61B 5/0035* (2013.01); *A61B 2576/00* (2013.01); *G06T 2207/10088* (2013.01); *G06T 2207/10104* (2013.01)

(58) Field of Classification Search
CPC ..................................................... G01R 33/481
See application file for complete search history.

(56) References Cited

U.S. PATENT DOCUMENTS 8,195,417 B2 * 6/2012 Feiweier ................ A61B 6/032 702/95
8,355,551 B2 * 1/2013 Thielemans .......... G06T 11/005 378/12

(Continued)

OTHER PUBLICATIONS

Dikaios et al., "MRI-based motion correction of thoracic PET: initial comparison of acquisition protocols and correction strategies suitable for simultaneous PET/MRI systems", Eur Radiol (2012) 22:439-446.*

(Continued)

*Primary Examiner* — Soo Park
(74) *Attorney, Agent, or Firm* — Peter R. Withstandley (57) ABSTRACT

A method of attenuation correction for a positron emission tomography (PET) system includes obtaining PET scan data representative of a volume scanned by the PET system, obtaining a plurality of magnetic resonance (MR) scan data sets representative of the volume, each MR scan data set being acquired in a respective time period during acquisition of the PET scan data by the PET system, detecting motion of the volume that occurred during the acquisition of the PET scan data based on an assessment of the plurality of MR scan data sets, the PET scan data, or the plurality of MR scan data sets and the PET scan data, determining attenuation correction data from the plurality of MR scan data sets based on the detected motion for alignment of the attenuation correction data and the PET scan data, and correcting the PET scan data with the attenuation correction data.

13 Claims, 3 Drawing Sheets

(51) Int. Cl.
*G06T 5/00* (2006.01)
*G06T 5/50* (2006.01)
*A61B 6/00* (2006.01)

(56) References Cited

U.S. PATENT DOCUMENTS

| | | | | |
|---|---|---|---|---|
| 8,768,432 B2* | 7/2014 | Ladebeck | ............... | A61B 5/055 324/309 |
| 2010/0268063 A1* | 10/2010 | Schmidt | ............... | G01R 33/481 600/411 |
| 2011/0123083 A1* | 5/2011 | Ojha | ..................... | G01N 24/08 382/131 |
| 2011/0230755 A1* | 9/2011 | MacFarlane | ............ | A61B 5/055 600/414 |
| 2011/0284751 A1* | 11/2011 | Klinder | ..................... | G06T 5/50 250/363.03 |
| 2012/0078089 A1* | 3/2012 | Wollenweber | ....... | A61B 6/5258 600/427 |
| 2012/0169333 A1* | 7/2012 | Katscher | ............... | G06T 7/2033 324/301 |
| 2013/0101193 A1* | 4/2013 | Ra | ........................ | G06T 11/005 382/131 |
| 2014/0099009 A1* | 4/2014 | Lonn | ..................... | G06T 11/005 382/131 |
| 2014/0133717 A1* | 5/2014 | Kabus | .................. | A61B 6/5264 382/128 |

OTHER PUBLICATIONS

Chun et al., "MRI-based nonrigid motion correciton in simultaneous PET/MRI", The Journal of Nuclear Medicine, vol. 53, No. 8, Aug. 2012.*
Bardera et al., "High-Dimensional Normalized Mutual Information for Image Registration Using Random Lines," WBIR, LNCS 4057, pp. 264-271 (2006).
Maes et al., "Medical Image Registration Using Mutual Information," Proc. of the IEEE, vol. 91, No. 10, pp. 1699-1722 (2003).
Meyer et al, "Demonstration of accuracy and clinical versatility of a mutual information for automatic multimodality image fusion using affine and think plate spline warped geometric deformations", Med. Image Anal 1(3): 195-206, 1997.
Studholme et al., "An overlap invariant entropy measure of 3D medical image alignment," Pattern Recognition Society, vol. 32, pp. 71-86 (1999).

* cited by examiner

| MRAC 1 | DIAG MR 1 | DIAG MR 2 | MRAC 2 | DIAG MR 3 | MRAC 3 |
|--------|-----------|-----------|--------|-----------|--------|
| PET ACQUISITION ||||||

FIG. 3

| MRAC 1 | MRAC 2 | MRAC 3 | MRAC 4 | MRAC 5 | MRAC 6 | MRAC 7 | MRAC 8 | MRAC 9 |
|--------|--------|--------|--------|--------|--------|--------|--------|--------|
| PET ACQUISITION |||||||||

FIG. 4

| MRAC 1 | DIAG MR 1 | DIAG MR 2 | MRAC 2 | DIAG MR 3 | MRAC 3 |
|--------|-----------|-----------|--------|-----------|--------|
| PET LIST-MODE ACQUISITION ||||||
| PET BIN 1 | PET BIN 2 | PET BIN 3 | PET BIN 4 | PET BIN 5 | PET BIN 6 | PET BIN 7 | PET BIN 8 |

MR SCAN SELECTION FOR PET ATTENUATION CORRECTION

CROSS-REFERENCE TO RELATED APPLICATION

This application claims the benefit of U.S. provisional application entitled "System for Processing Corresponding MR and PET Image Data," filed Dec. 4, 2012, and assigned Ser. No. 61/733,132, the entire disclosure of which is hereby incorporated by reference.

BACKGROUND

The present embodiments relate to integration of imaging systems, specifically magnetic resonance (MR) imaging and positron emission tomography (PET) systems.

PET imaging yields quantitative measures of metabolic and dynamic processes. PET imaging relies on the positron emitting decay of a radioactive tracer isotope attached to a biologically active compound. The subsequent annihilation of the positrons with electrons generates pairs of high-energy photons travelling near opposite directions. These events are detected when the photons reach a detector of the PET system. Unfortunately, the photons can be absorbed by tissue, particularly bone. This absorption is referred to as attenuation and leads to an undesirable intensity distortion in PET images.

Raw PET data is often corrected for photon attenuation and scatter. Attenuation correction typically uses data acquired from a separate measurement. One common approach uses computed tomography (CT) data provided by a combined PET/CT scanner. Other clinical scanners provide concurrent PET and magnetic resonance (MR) imaging. Use of MR data for attenuation correction advantageously avoids the radiation dose involved in CT scans. A typical MR/PET workflow may thus begin with concurrent PET scanning and MR scanning for attenuation correction. After the MR attenuation correction scan is complete, further MR scanning is often conducted for diagnostic purposes while the PET scan continues.

Patient motion during PET acquisition complicates attenuation correction. If there is patient motion during the PET scanning, the lack of spatial registration between PET and MR attenuation correction data may result in poor image quality. If an operator of the MR/PET system is made aware of the patient motion, another MR attenuation correction scan may be conducted at the end of the PET scan. The operator then visually compares non-attenuation corrected PET images with the two MR attenuation correction scans to manually select the MR data to be used for attenuation correction of the PET data. This approach is undesirably time consuming and subjective.

SUMMARY

By way of introduction, the embodiments described below include systems, computer program products, and methods for attenuation correction of positron emission tomography (PET) scan data. Attenuation correction data is aligned with PET scan data as determined from a plurality of magnetic resonance (MR) scan data sets, the use of which is based on motion detected during acquisition of the PET scan data. The motion may be detected based on an assessment of the plurality of MR scan data sets themselves or on differences between each MR scan data set and other scan data, such as the PET scan data or further MR scan data acquired during the acquisition of the PET scan data.

In a first aspect, a method of attenuation correction for a PET system includes obtaining PET scan data representative of a volume scanned by the PET system, obtaining a plurality of MR scan data sets representative of the volume, each MR scan data set being acquired in a respective time period during acquisition of the PET scan data by the PET system, detecting, with a processor, motion of the volume that occurred during the acquisition of the PET scan data based on an assessment of the plurality of MR scan data sets, the PET scan data, or the plurality of MR scan data sets and the PET scan data, determining, with the processor, attenuation correction data from the plurality of MR scan data sets based on the detected motion for alignment of the attenuation correction data and the PET scan data, and correcting the PET scan data with the attenuation correction data.

In a second aspect, a computer program product for attenuation correction for a PET system includes one or more computer-readable storage media having stored thereon computer-executable instructions for execution by one or more processors of a computing system to cause the computing system to perform operations. The operations include obtaining PET scan data representative of a volume scanned by the PET system, obtaining diagnostic MR scan data of the volume, the diagnostic MR data being acquired during acquisition of the PET scan data by the PET system, obtaining a plurality of MR attenuation correction (MR-AC) scan data sets representative of the volume, each MR-AC scan data set being acquired during the acquisition of the PET scan data by the PET system when the diagnostic MR scan data is not being acquired, detecting motion of the volume that occurred during the acquisition of the PET scan data based on a spatial alignment assessment of the plurality of MR-AC scan data sets, the PET scan data, the diagnostic MR scan data, or combinations thereof, determining attenuation correction data from the plurality of MR-AC scan data sets based on the detected motion for alignment of the attenuation correction data and the PET scan data, and correcting the PET scan data with the attenuation correction data.

In a third aspect, a data processing system for attenuation correction for a PET system includes a data store in which PET scan data representative of a volume scanned by the PET system is stored, and in which a plurality of MR attenuation correction (MR-AC) scan data sets representative of the volume are stored, each MR-AC scan data set being acquired during acquisition of the PET scan data by the PET system when diagnostic MR scan data is not being acquired. The data processing system further includes a processor coupled to the data store and configured to detect motion of the volume that occurred during the acquisition of the PET scan data based on a spatial alignment assessment of the plurality of MR scan data sets, the PET scan data, or the plurality of MR scan data sets and the PET scan data. The processor is further configured to determine attenuation correction data from the plurality of MR scan data sets based on the detected motion for alignment of the attenuation correction data and the PET scan data. The processor is further configured to correct the PET scan data with the attenuation correction data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PRESENTLY PREFERRED EMBODIMENTS

Methods, computer program products, and systems for attenuation correction of PET scan data are described. Multiple MR scan data sets are acquired over the duration of the PET acquisition for purposes of attenuation correction (AC). The MR scan data sets may be acquired at intervals during the PET acquisition. The acquisition of the MR-AC scan data sets may advantageously not involve as much time as a full MR data collection (e.g., a diagnostic MR scan). Magnetic resonance AC (MR-AC) data is determined from the plurality of MR scan data sets based on the detection of motion of the volume scanned during the PET acquisition. Motion is detected based on an assessment, e.g., an assessment of spatial alignment, of scan data acquired during the PET acquisition. With knowledge of when the motion occurred during the PET acquisition, the MR-AC data may be selected or otherwise determined for alignment with the PET scan data. The MR-AC data may thus be naturally aligned with the PET scan data. Improved PET imaging may thus be provided, while avoiding visual comparisons and other user intervention or other processing, including, for instance, the use of registration algorithms to align MR-AC data with PET scan data.

The disclosed embodiments may support longer PET acquisitions. The quality of PET scan data may improve with longer acquisition times. With longer acquisition times, however, it is more likely that movement occurs during the PET acquisition. The disclosed embodiments may provide a technique for correcting the PET scan data despite the occurrence of such movement.

Automated and objective selection or other determination of MR-AC data is implemented. Improved or better alignment of PET and MR-AC data may be achieved. With the MR-AC data better aligned with the PET scan data, the attenuation correction of the PET scan data may yield more accurate or optimized PET quantification.

In some embodiments, the spatial alignment assessment is used to select one of the plurality of MR scan data sets for use as the MR-AC data. The best data set of the plurality of MR-AC scan data sets may be automatically selected as the MR-AC data. For example, if two of the MR-AC scan data sets are aligned nicely, and the time between the sets is sufficient, then one or both of the sets may be used for attenuation correction. Using the best of multiple MR-AC scans distributed over the duration of the PET acquisition may be more effective than simply using the data from an MR-AC scan at either the beginning or the end of the PET acquisition. An MR-AC scan during the PET acquisition may have better spatial alignment with the PET scan data due to motion of the patient volume at some point during the PET acquisition.

In other embodiments, the MR-AC data is determined from a combination of multiple MR-AC scan data sets. For example, an interpolation, average, or other function is used to determine the MR-AC data from two or more MR-AC data sets.

The attenuation correction techniques may include feedback to an operator of the MR/PET system. The feedback may be provided during the PET acquisition to suggest that an additional MR-AC scan is warranted for a given bed position. Acquisition of an additional MR-AC scan data set may be warranted if, for instance, patient motion exceeds a threshold. Alternatively, the threshold may be used to determine that one of the previously acquired MR-AC data sets would constitute a more optimal MR-AC scan data set due to the excessive patient motion.

Different scan data may be assessed to detect motion in support of the alignment of the MR-AC data with the PET scan data. The assessment may be between pairs of the plurality of MR scan data sets or between each MR scan data set and other scan data acquired during the PET acquisition. In one embodiment, the other scan data is diagnostic MR scan data. In another embodiment, the other scan data is the PET scan data. In other embodiments, the assessment may be between bins of the PET scan data.

The disclosed methods and systems are not limited to particular scan sequences for the MR and PET systems. The number, timing, and other characteristics of the MR-AC scans may vary. Diagnostic MR scans may, but need not, be included. The diagnostic MR scans may have a higher spatial resolution than the MR-AC scans. The use of diagnostic MR scan data may be useful as provide additional data for detecting motion during the PET acquisition. The number, timing, and other characteristics of diagnostic MR scans may also vary.

The disclosed methods and systems are not limited to use with any particular MR system or PET system. For example, the disclosed embodiments are not limited to a particular type of primary magnet for the MR system. The MR system need not include a cryomagnet or superconducting or other electromagnet. The MR system may have a tunnel or open configuration. The PET system may have any number of PET detectors. Other characteristics of the MR and PET systems may also vary, including the manner in which the systems are integrated with one another.

In some embodiments, the MR-AC scan data sets may be used to build a model of the motion. A physiological signal from a monitor of the respiration of the patient may then be used to select the MR-AC scan data set that applies to the respiratory phase for the PET scan data. The MR-AC scan data and/or the PET scan data may be used to determine the applicable phase of the model. The MR-AC scan data sets may alternatively or additionally be used to update the motion model through projections of the principle components of the motion. Such updates may be useful in cases in which the breathing pattern of the patient changes.

The differences in the MR-AC scan data sets may be used to estimate how and when the motion occurs in the patient. This information, which may be referred to as a motion field, may be used to improve the PET reconstruction resolution and contrast in addition to supplying information useful for attenuation correction.

Figure 1:
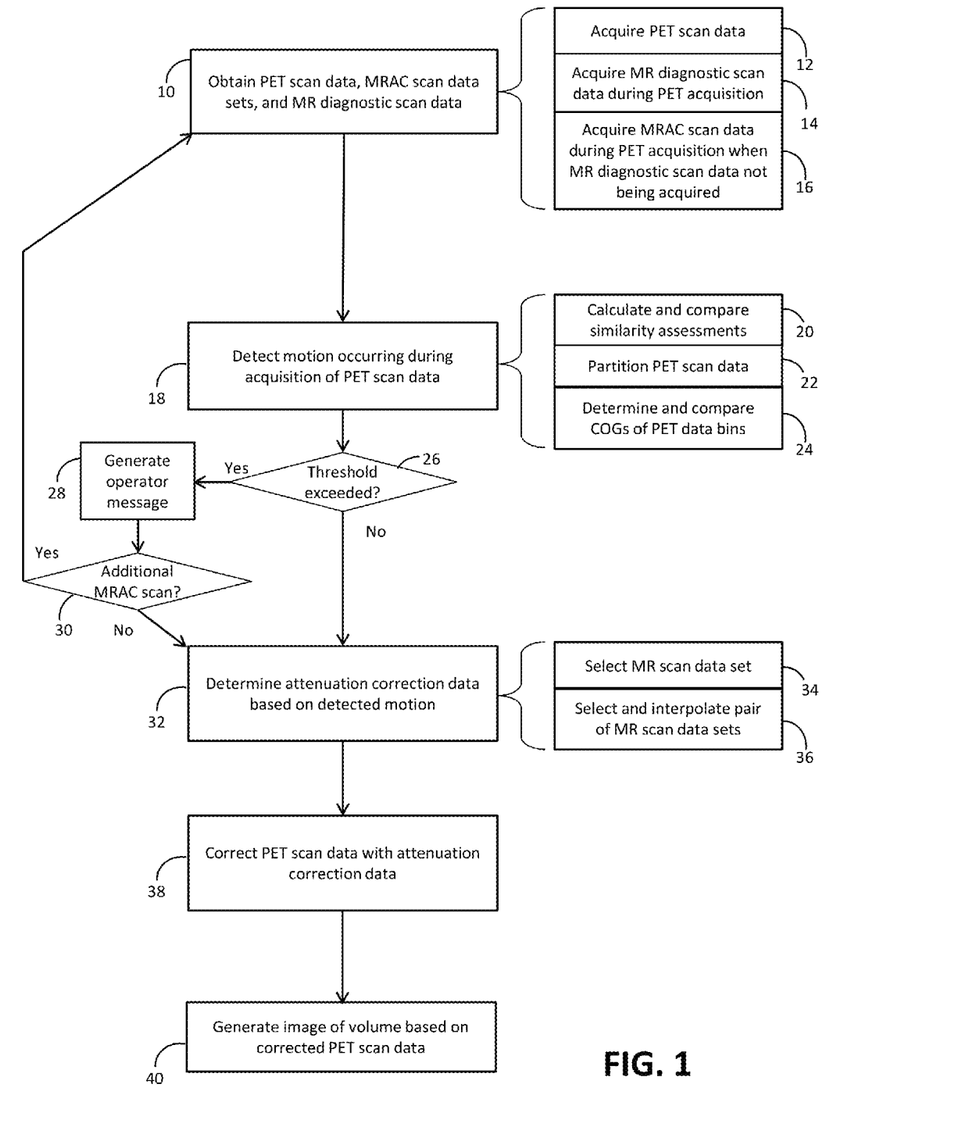
FIG. 1 is a flow diagram of one embodiment of an attenuation correction method.

FIG. 1 depicts an attenuation correction method in accordance with one embodiment. The method is directed to correcting PET scan data acquired by a PET system. The attenuation correction is based on MR-AC scan data acquired during the acquisition of the PET scan data. Additional, fewer, or alternative acts may be included in the method. For example, diagnostic MR data may not be acquired during acquisition of the PET scan data.

The PET scan data and MR scan data is obtained in act 10. The PET scan data is representative of a volume scanned by the PET system. The act 10 may include acquisition of the PET scan data in act 12. In other cases, the PET scan data is previously acquired. The MR scan data includes a plurality of MR scan data sets also representative of the volume. Each MR scan data set may be acquired in a respective time period during acquisition of the PET scan data by the PET system. The MR scan data sets are distributed throughout the PET acquisition. Examples are provided in connection with FIGS. 3-5. Each MR scan data set of the plurality of MR scan data sets may be acquired via an MR scan sequence configured to support the attenuation correction of the PET scan data. In such cases, each MR scan data set may accordingly be referred to as an MR-AC scan data set.

The MR scan data may include diagnostic and non-diagnostic MR scan data. The MR scan(s) for the diagnostic MR scan data are configured to provide scan data suitable for use in diagnosis rather than attenuation correction. The MR scans for the non-diagnostic MR scan data are configured to provide MR-AC scan data sets. In this embodiment, diagnostic MR scan data is acquired in act 14 during the PET acquisition. The non-diagnostic MR scan data or MR-AC scan data sets may be acquired during the PET acquisition in act 16 when the diagnostic MR scan data is not being acquired. In other cases, diagnostic MR scan data is not acquired. MR-AC scan data for attenuation correction may be acquired continuously or throughout the PET acquisition in such cases.

Multiple MR-AC scan data sets are obtained for each bed position. At least two MR-AC scans are acquired for each position in which the volume is scanned by the PET system. The best or optimal MR-AC scan data set is selected or otherwise determined as described below.

Act 10 may include accessing or otherwise obtaining previously acquired scan data. Act 10 may thus not include data acquisition or scanning operations directed thereto. For example, the PET scan data and/or MR scan data may be obtained from a data store during implementation of the method. The PET scan data and/or MR scan data may thus be acquired or generated independently of, or in conjunction with, the implementation of the method.

In act 18, motion of the volume during the acquisition of the PET scan data is detected. The processing directed to detecting the motion may be implemented at any point after the acquisition, including, for example, after obtaining the PET and other scan data from a data store. The motion is detected based on an assessment of the scan data acquired or otherwise obtained during the PET acquisition. The assessment may be or include a spatial alignment assessment involving one or more of the types of scan data acquired during the PET acquisition. The spatial alignment of one or more anatomical features may be assessed or quantified. For example, motion may be detected via landmarks in different images. Alternatively or additionally, offsets between sets of landmarks may be compared to detect motion.

In some embodiments, the plurality of MR scan data sets, or MR-AC data, are assessed alone. In other embodiments, the plurality of MR scan data sets are assessed with the PET scan data. In yet other embodiments, the assessment involves evaluating or comparing the plurality of MR scan data sets and the diagnostic MR scan data. In still other embodiments, the plurality of MR scan data sets and the PET scan data are evaluated in the assessment. In still further embodiments, the PET scan data is assessed alone. In these and other cases, motion is detected through the detection of the degree to which scan data is aligned or misaligned.

The assessment to detect motion may include an act 20 in which similarity measurements are calculated and compared. In some cases, for example, a similarity measurement is calculated for each MR-AC scan data set of the plurality of MR-AC scan data sets. In one embodiment, the motion may be detected by calculating a similarity measurement between each pair of the plurality of MR-AC scan data sets. The calculated similarity measurements may then be compared with one another to identify a time period during which the motion occurred. Motion may be detected by assessing where the similarity measurement(s) for the MR scan data sets are higher. For example, as shown in the exemplary scan sequences of FIG. 3 and FIG. 4, if the similarity measurement for MR-AC scan data sets MRAC 1 and MRAC 2 is higher than the similarity measurement for MR-AC scan data sets MRAC 2 and MRAC 3, then motion may have occurred between (and/or during) the acquisition of the second and third MR-AC scan data sets. As described below, the MR-AC scan data set MRAC 1 and/or the MR-AC scan data set MRAC 2 may then be deemed to be most aligned with the PET scan data and accordingly selected to determine data to be used for attenuation correction of the PET scan data.

The similarity measurement calculation may include computing a normalized mutual information (NMI) measurement. The NMI measurement is computed between two images (e.g., image M and image N) as follows:

$H(M)$=marginal entropy for image $M$ $H(N)$=marginal entropy for image $N$ $Y(M,N)$=normalized mutual information between images $M$ and $N$ $Y(M,N)=(H(M)+H(N))/H(M,N)$ Other cost measures or measurements of alignment may be used, including, for example, normalized cross correlation and local cross correlation, which, like the NMI measurement, may be useful in cross-modality and other assessments presenting differences in contrast. Examples of cross-modality assessments are provided below. A wide variety of other similarity measurements may be used in non-cross-modality assessments that include, for instance, the comparison of two MR-AC scan data sets. For example, sum of squares and other measures may be used.

In other embodiments, the similarity measurements may include measurements calculated for each MR-AC scan data set relative to other types of scan data acquired during the PET acquisition. For example, similarity measurements may be calculated for each MR-AC scan data set relative to diagnostic MR scan data acquired during the PET acquisition. As shown in the exemplary scan sequence of FIG. 3, three diagnostic MR scans, DIAG MR 1, DIAG MR 2, and DIAG MR 3, are implemented during the PET acquisition. Three MR-AC scan data sets, MRAC 1, MRAC 2, and MRAC 3, are acquired when the diagnostic MR scan data is not being acquired. In one exemplary embodiment, an MR scan at the desired latency relative to the PET acquisition (e.g., diagnostic MR scan DIAG MR 2) may be selected as a target. Similarity measurements may then be calculated for each MR-AC scan relative to the target to quantify the alignment between the respective MR-AC scan and the desired time point of the PET acquisition. The MR-AC scan with the best alignment to the target may be automatically selected. Other techniques for co-registration of the MR-AC scan data sets to one or more diagnostic MR scans may be implemented. For example, alignment with more than one target may be evaluated. Other embodiments may not involve a target diagnostic MR scan.

Similarity measurements involving the diagnostic MR scans may be useful in cases in which, for instance, the diagnostic MR scans may occupy a considerable amount of time during the PET acquisition. The similarity measurements may also be calculated for the diagnostic MR scans to provide further insight into when motion may have occurred.

Similarity measurements may alternatively or additionally be calculated for each respective MR scan data set relative to the PET scan data. The PET scan data may be non-attenuation-corrected, or raw, PET scan data. The PET scan data may be useful in this regard if the anatomy is sufficiently distinguished from background. For instance, PET scan data acquired using a tracer having significant skin uptake may be used. In these embodiments, the MRAC scan data set(s) having the best (e.g., highest) similarity measurement with the PET scan data may be selected or otherwise used to determine the data to be used for attenuation correction. The attenuation correction data and the PET scan data may thus be co-registered.

Figure 5:
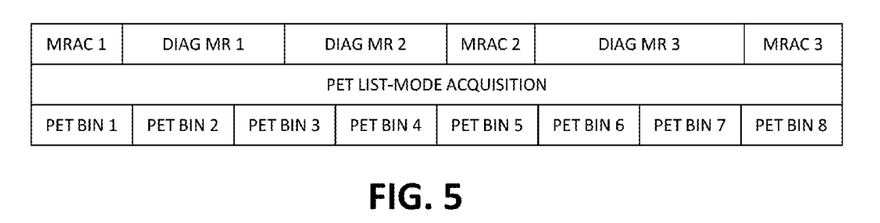

The detection of motion may include assessments not involving the MR-AC scan data sets. For example, the motion detection may include an act 22 in which the PET scan data is partitioned into a plurality of PET data bins. An example of such partitioning is shown in FIG. 5. Each bin corresponds with a respective time segment of the PET acquisition. The PET scan data may be partitioned while formatted as list-mode data. List-mode PET acquisition offers the ability to retrospectively reconstruct a PET acquisition into multiple time bins. Motion may then be detected in an act 24 in which the PET scan data in each bin is processed to extract motion information. In one embodiment, the PET scan data in each bin is assessed to determine patient motion over time. For example, a best fitting attenuation map may be used for each bin. The MR-AC scan data set(s) associated with the longest time period without motion may then be selected.

In some embodiments, a center of gravity of each PET data bin is determined and compared with the centers of gravity of other bins to identify a time period during which the motion occurred. One or more MR-AC scan data sets may then be selected to determine the data to be used for attenuation correction based on when the motion occurred.

The center of gravity of each PET data bin may vary as a result of respiration, cardiac motion, bowel gas movement, bladder filling, contrast agent motion, or other non-gross motion of the patient. The center of gravity information may be used to determine which bins are aligned and/or not aligned with one another. Different attenuation correction data may then be determined for the various bins or groups of bins. Different MR-AC scan sets may accordingly be used to correct the PET scan data for different bins. Embodiments in which multiple PET images are reconstructed over time in order to view tracer uptake and/or other dynamics may benefit from maximizing alignment with each PET image (e.g., bin).

Other embodiments involving PET data bins may involve the MR-AC scan data sets in detecting motion. For example, one or more similarity measurements may be calculated for each PET data bin based on the plurality of MR-AC scan data sets. With reference to the example of FIG. 5, the similarity measurements involving MR-AC scan data set MRAC 2 may reveal that motion occurred during PET Data Bin 6. The attenuation correction data may then be selected or determined accordingly, as described below.

The similarity measurement comparisons may be useful in embodiments in which the motion is detected in real-time, i.e., during the PET acquisition. In the embodiment of FIG. 1, the comparison of the similarity measurements is analyzed in a decision block 26 to determine whether a threshold is exceeded. The threshold may be indicative of a significant amount of motion. If the subject moves too much, the threshold is exceeded, and control may pass to an act 28 in which an alert or other message is generated or otherwise initiated to an operator. The message may prompt the operator to remind the patient to refrain from movement. The message may alternatively or additionally prompt the operator or system to acquire one or more additional MR-AC scan data sets. If a decision to acquire an additional MR-AC scan data set is made, a decision block 30 returns control to the act 10. If not, then the method may continue with either further motion detection or proceed with determination of the attenuation correction data as shown in FIG. 1. Additional or alternative feedback may be provided via the messages.

The feedback may be provided via automatically generated, spoken commands. The commands may be directed to the operator or the patient. The feedback may be useful in those scenarios where the motion may not otherwise be noticed during the PET acquisition.

Alternative or additional feedback may be provided, including visual feedback regarding the motion detected. For example, an interface may be generated that depicts when motion occurs, when a threshold has been exceeded, and/or when an MR-AC data scan set fails (e.g., due to insufficient alignment). The interface may depict start and end times of the various data scans over the duration of the PET acquisition. Each scan may be depicted with various options and/or information. For example, the user may deselect or otherwise remove MR-AC data scan sets from consideration, interpolate MR-AC data scan sets, or modify the scan sequence to address the occurrence of the motion. The user interface may alternatively or additionally provide, in the presence of motion, an option to the operator to select one or more MR-AC scan data sets for use in attenuation correction.

The data to be used for attenuation correction is determined in an act 32. The attenuation correction data is determined from the plurality of MR scan data sets. One or more of the MR scan data sets are selected for the determination based on the detected motion. Using information on the detected motion, the MR scan data set(s) most or best aligned with the PET scan data may be selected for use in the determination. For example, the attenuation correction data may be determined by selecting one or more MR-AC scan data sets acquired outside of the time period(s) identified during the motion detection procedure. Alignment of the attenuation correction data and the PET scan data may thus be achieved.

In some cases, determining the attenuation correction data includes an act 34 in which a single MR-AC scan data set of the plurality of MR-AC scan data sets is selected. The single MR scan data set may be one of the data sets acquired outside of the time period(s) identified in act 18, i.e., the time period(s) in which motion is detected. The MR-AC scan data set(s) associated with the longest period of time without motion may be selected. For example, if motion was not detected between two MR-AC scan data sets separated by a sufficient duration of time (e.g., the scan data sets were acquired five minutes apart), one or both of the scan data sets may be considered the optimal scan data set (or used to determine the optimal scan data set). Alternatively or additionally, the MR-AC scan data set of the plurality of MR-AC scan data sets most aligned with other scan data, such as the diagnostic MR scan data or the PET scan data, based on the calculated similarity measurements may be selected.

In other embodiments, multiple MR-AC scan data sets are used to determine the attenuation correction data. For example, determining the attenuation correction data may include an act 36 in which a pair of MR-AC scan data sets of the plurality of MR scan data sets is selected. The pair of MR-AC scan data sets may be acquired outside of the time period identified in act 18, i.e., the time period(s) in which motion is detected. The attenuation correction data may then be determined by interpolating between the pair of MR-AC scan data sets. Interpolation may be useful if gross body movement is not occurring, including, for instance, addressing different respiratory phases with different MR-AC scan data sets. Techniques other than interpolation may be used, including, for example, averaging. The use of multiple MR-AC scan data sets may be useful in situations in which, for example, motion is detected between two MR-AC scans determined to be the best of the plurality of MR-AC scans, but it is difficult to determine which of the two scans is more aligned with the PET scan data.

In embodiments in which the PET scan data has been divided up into bins or timeframes (e.g., via list-mode data), attenuation correction data may be selected or otherwise determined for each bin or timeframe. Any one of the above-described methods of selecting or determining the attenuation correction data may be used for each timeframe. In one embodiment, for example, the MR-AC scan data set most aligned with a respective PET scan data of a particular PET data bin is selected. The alignment may be determined via a similarity measurement as described above. The selection process is repeated for each PET data bin.

Alternatively or additionally, the PET scan data from the PET data bins may be combined based upon when the motion is detected. For example, with reference to FIG. 5, if the assessment reveals that the patient moved during the acquisition of PET Bin 2 and during the acquisition of PET Bin 8, then the PET scan data from PET Bin 3 through PET Bin 7 may be combined. The MR-AC scan data set that falls within that time period, i.e., MR-AC scan data set MRAC 2, may then be selected for use as the attenuation correction data. A different MR-AC scan data set may potentially provide the attenuation correction data for each bin. Other techniques for determining the attenuation correction data may be used, as described above, if, for instance, multiple MR-AC scan data sets were acquired during the time period. The manner in which the motion is detected may vary, as described above.

Multiple groups of PET data bins may be used. For example, one group of PET data bins may precede a first occurrence of motion, another group of PET data bins may be disposed between the first occurrence and a second occurrence, and a final group of PET data bins may be subsequent to the second occurrence. Attenuation correction data may be determined separately for each grouping or in common across groupings.

In act 38, the PET scan data is corrected with the attenuation correction data. Any now known or hereafter developed attenuation correction procedure may be used. An image of the scanned volume may then be generated in act 40 based on the corrected PET scan data. Alternatively or additionally, the corrected PET scan data may be stored in a data store for later display or use.

The order in which the acts of FIG. 1 are performed may vary from the example shown. Some or all of the acts may be implemented concurrently or in parallel. For example, the detection of motion and/or calculation of similarity assessments may begin while scan data is still being acquired.

Figure 2:
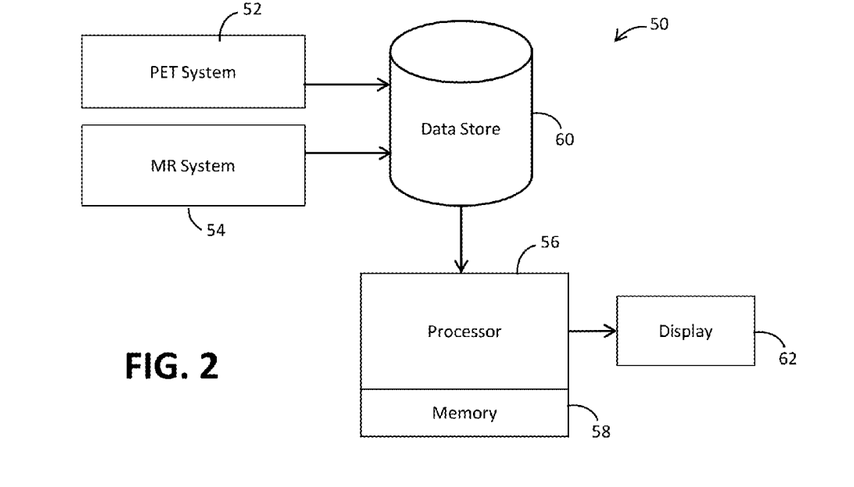
FIG. 2 is a block diagram of a data processing system for implementing the method of FIG. 1 in accordance with one embodiment.

FIG. 2 depicts an exemplary system 50 configured to facilitate the implementation and/or application of the disclosed attenuation correction techniques. In this example, the system 50 includes a PET system 52, an MR system 54, a processor 56, a memory 58, a data store 60, and a display 62. The system 50 may include additional, fewer, or alternative components. For example, the memory 58 and the data store 60 may be integrated into a single memory. One or more user interfaces (e.g., user consoles) for data input and control of the PET and MR systems 52, 54 may be provided.

A subset of the system 50 may be configured as a data processing system configured for attenuation correction of the PET scan data acquired by the PET system 52. For example, the data processing system may include the components of the system 50 not directed to acquisition of scan data.

Scan data acquired by the PET system 52 and the MR system 54 is stored in the data store 60. The scan data includes PET scan data representative of a volume scanned by the PET system 52 as described above. The scan data further includes a plurality of MR-AC scan data sets representative of the volume. Each MR-AC scan data set is acquired by the MR system 54 during acquisition of the PET scan data. The scan data may further include diagnostic MR scan data acquired by the MR system 54 during one or more diagnostic scans. In those cases, each MR-AC scan data set is acquired by the MR system 54 when the diagnostic MR scan data is not being acquired. For example, an MR-AC scan data set may be acquired wherever there is a break in the diagnostic MR scanning.

The processor 56 is coupled to the data store 60 to access the scan data. The data store 60 may be accessed at any point after the storage of the scan data to obtain the scan data in support of implementing the attenuation correction procedures described herein. The nature of the communication link between the processor 56 and the data store 60 may vary. For example, the processor 56 and the data store 60 may be disposed in a common computing device, connected via a local area network, or communicating via a wide-area or other distributed network.

The processor 56 is configured, e.g., via one or more instruction sets, to detect motion of the volume that occurred during the acquisition of the PET scan data. The motion may be detected based on a spatial alignment or other assessment of the scan data stored in the data store 60. As described above, the processor 56 may detect motion through an assessment of the plurality of MR scan data sets, the PET scan data, or the plurality of MR scan data sets and the PET scan data. The assessment may include the calculation of similarity measurements. Normalized mutual information and other similarity measurements may be used to accommodate cross-modality comparisons, as described above. For example, a similarity measurement may be calculated by the processor 56 for each MR scan data set of the plurality of MR scan data sets.

The processor 56 is further configured to determine attenuation correction data from the plurality of MR scan data sets based on the detected motion for alignment of the attenuation correction data and the PET scan data. The manner in which the attenuation correction data is determined may vary as described above. For example, the attenuation correction data may be determined through selection of one or more of the MR-AC scan data sets. In cases involving multiple MR-AC scan data sets, the attenuation correction data may be determined through interpolation and/or other algorithms configured to combine the MR-AC scan data sets.

The processor 56 is further configured to correct the PET scan data with the attenuation correction data, as described above. In some cases, the processor 56 may also be configured to render one or more images of the corrected PET scan data via the display 62. Alternatively or additionally, the corrected PET scan data may be stored in the data store 60 and/or other data store for later use or display.

The processor 56 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position and/or generating images. The processor 56 is a single device or multiple devices operating in serial, parallel, or separately. The processor 56 may have any number of processing cores distributed over one or more devices. For example, the disclosed methods may be implemented by a pair of central processing units (CPUs) having a total of four processing cores. The processor 56 may be a main processor of a computer, such as a laptop or desktop computer, or may be a processor for handling some tasks in a larger system, such as in an imaging system.

The memory 58 is a graphics processing memory, video random access memory, random access memory, system memory, cache memory, hard drive, optical media, magnetic media, flash drive, buffer, database, combinations thereof, or other now known or later developed memory device for storing data or video information. The memory 58 is part of an imaging system, part of a computer associated with the processor 56, part of a database, part of another system, or a standalone device.

The acts described in connection with FIGS. 1 and 2 may be implemented via instructions executed by the programmed processor 56. Data representative of the instructions may be stored in the memory 58 or any other memory. The acts may be implemented by one or more processors and one or more memories in addition or alternative to the processor 56 and the memory 58. The instructions may include computer code to direct the processor 56 or other processor(s) to perform the acts described above. Additional, fewer, or different operations or acts may be implemented. For example, the operations may include accessing scan data from the data store 60.

The memory 58 or other memory may include a non-transitory computer readable storage medium storing data representing instructions executable by the programmed processor 56. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, and parallel processing, as described above.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

Additional, fewer, or different components may be provided. For example, a network or network connection may be provided, such as for networking with a medical imaging network or data archival system. One or more user inputs or other user interfaces may be provided.

The configuration of the PET system 52 may vary. For example, the PET system 52 may include any number of PET detectors. The configuration of each PET detector may also vary. For example, the PET detectors may be whole body detectors. Any now known or later developed PET imaging system components may be used.

The configuration of the MR system 54 may vary. For example, the configuration of a main magnet and gradient coils of the MR system 54 may vary. The manner in which the MR system 54 is integrated with the PET system 52 may also vary. For example, some parts of the MR system 54 may be provided within a common housing shared by components of the PET system 52. Any now known or later developed MR imaging system components may be used.

Figure 3:
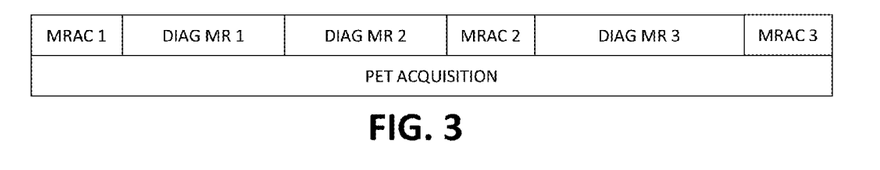
FIGS. 3-5 are timing diagrams of concurrent MR and PET scan sequences for use in the method of FIG. 1 or by the system of FIG. 2 in accordance with several embodiments.

FIG. 3 depicts one example of a scan sequence implemented by the system 50 (FIG. 2) or via the method of FIG. 1. The scan sequence may correspond with a single table or patient position. Additional scan sequences may be provided for other positions.

The scan sequence includes multiple MR-AC scans during a PET acquisition. Rather than merely a single MR-AC scan at the beginning (and/or at the end) of the PET acquisition, a total of three MR-AC scans are performed during the PET acquisition. The timing of the MR-AC scans may vary. For example, an MR-AC scan data set may be acquired automatically and/or periodically whenever the MR system 54 (FIG. 2) is idle. In some cases, an MR-AC scan data set is acquired whenever the MR system 54 is not implementing a diagnostic scan.

Figure 4:
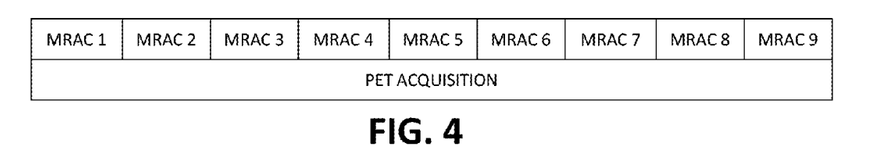

FIG. 4 depicts one example of a scan sequence in which the MR system 54 (FIG. 2) does not acquire diagnostic scan data. In such cases, the system 50 may be configured to continuously or periodically acquire MR-AC scan data as shown.

FIG. 5 depicts one example of a scan sequence in which list-mode data acquired by the PET system 52 (FIG. 2) is divided up into timeframes or bins. The PET scan data for each bin may be used to detect motion and/or determine attenuation correction data as described above. Alternatively or additionally, the PET scan data for each bin may be corrected by individually or collectively, as described above.

Figure 6:
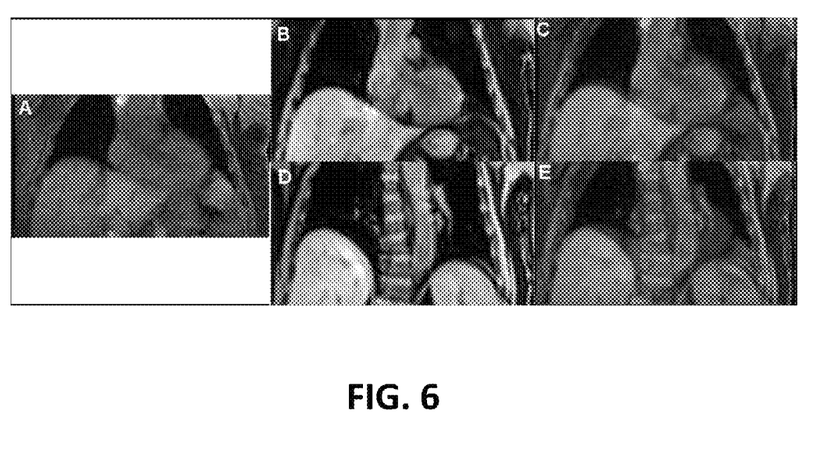
FIG. 6 are examples of images generated from MR attenuation correction scan data sets for attenuation correction of PET scan data concurrently acquired with diagnostic MR scan data in accordance with one embodiment.

FIG. 6 depicts a diagnostic MR scan A used as a reference for attenuation correction alignment in accordance with one or more of the disclosed embodiments. MR-AC scans B and D are compared with the reference scan A. An overlay C of the reference scan A and the MR-AC scan B shows better alignment than an overlay E of the reference scan A and the MR-AC scan D. But rather than use a visual, subjective comparison of the overlays C and E, the MR-AC scan B is selected because the calculated alignment assessment, in this case NMI, between the MR-AC scan B and the reference is 0.18, which is greater than the NMI between the MR-AC scan D and the reference (NMI=0.16).

The disclosed embodiments support attenuation correction based on multiple MR-AC scan data sets. The disclosed embodiments provide a technique for automatically selecting one or more of the MR-AC scan data sets for use in determining the data to be used for attenuation correction. The technique may include a calculation, computation, or other process for quantifying the spatial alignment of scan data acquired during the PET acquisition. The quantification is used to detect motion during the PET acquisition. The technique may be configured such that the data to be used for attenuation correction is naturally aligned with the PET scan data. The MR-AC scan data set (or combination of multiple sets) having the best or optimal spatial alignment with the PET scan data may be determined. Visual inspection and/or registration of the MR-AC scan data sets may thus be avoided.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method of attenuation correction for a positron emission tomography (PET) system, the method comprising:
obtaining PET scan data representative of a volume scanned by the PET system;
obtaining a plurality of magnetic resonance (MR) scan data sets representative of the volume, each MR scan data set being acquired in a respective time period during acquisition of the PET scan data by the PET system;
detecting, with a processor, motion of the volume that occurred during the acquisition of the PET scan data based on an assessment of the plurality of MR scan data sets, the PET scan data, or the plurality of MR scan data sets and the PET scan data;
determining, with the processor, attenuation correction data from the plurality of MR scan data sets based on the detected motion for alignment of the attenuation correction data and the PET scan data; and
correcting the PET scan data with the attenuation correction data;
wherein detecting the motion comprises:
calculating a similarity measurement between each pair of the plurality of MR scan data sets, and
comparing the respective calculated similarity measurements to identify a time period during which the motion occurred; and
wherein determining the attenuation correction data comprises:
selecting a pair of MR scan data sets of the plurality of MR scan data sets acquired outside of the identified time period, and
interpolating between the pair of MR scan data sets to determine the attenuation correction data.

2. The method of claim 1, wherein determining the attenuation correction data comprises selecting an MR scan data set of the plurality of MR scan data sets acquired outside of the identified time period.

3. The method of claim 1, wherein detecting the motion comprises calculating a similarity measurement for each MR scan data set of the plurality of MR scan data sets.

4. The method of claim 3, wherein:
calculating the similarity measurement comprises calculating the similarity measurement for the respective MR scan data set relative to diagnostic MR scan data acquired during the acquisition of the PET scan data by the PET system; and
determining the attenuation correction data comprises selecting an MR scan data set of the plurality of MR scan data sets most aligned with the diagnostic MR scan data based on the calculated similarity measurements.

5. The method of claim 3, wherein:
calculating the similarity measurement comprises calculating the similarity measurement for the respective MR scan data set relative to the PET scan data; and
determining the attenuation correction data comprises selecting an MR scan data set of the plurality of MR scan data sets most aligned with the PET scan data based on the calculated similarity measurements.

6. The method of claim 3, wherein calculating the similarity measurement comprises computing a normalized mutual information (NMI) measurement.

7. The method of claim 1, wherein detecting the motion comprises partitioning the PET scan data into a plurality of PET data bins.

8. The method of claim 7, wherein:
detecting the motion comprises calculating, for each PET data bin, a similarity measurement based on the plurality of MR scan data sets; and
determining the attenuation correction data comprises selecting, for each PET data bin, an MR scan data set of the plurality of MR scan data sets based on the similarity measurement.

9. The method of claim 8, wherein selecting the MR scan data set comprises selecting, for each PET data bin, the MR scan data set of the plurality of MR scan data sets most aligned with the respective PET data bin based on the similarity measurement.

10. The method of claim 1, wherein each MR scan data set of the plurality of MR scan data sets is acquired via an MR scan sequence configured to support the attenuation correction of the PET scan data.

11. The method of claim 1, further comprising initiating an alert to an operator of the PET system regarding the detected motion.

12. A data processing system for attenuation correction for a positron emission tomography (PET) system, the data processing system comprising:
a data store in which PET scan data representative of a volume scanned by the PET system is stored, and in which a plurality of magnetic resonance (MR) attenuation correction (MR-AC) scan data sets representative of the volume are stored, each MR-AC scan data set being acquired during acquisition of the PET scan data by the PET system when diagnostic MR scan data is not being acquired; and
a processor coupled to the data store and configured to detect motion of the volume that occurred during the acquisition of the PET scan data based on a spatial alignment assessment of the plurality of MR scan data sets, the PET scan data, or the plurality of MR scan data sets and the PET scan data;
wherein the processor is further configured to determine attenuation correction data from the plurality of MR scan data sets based on the detected motion for alignment of the attenuation correction data and the PET scan data;
wherein the processor is further configured to correct the PET scan data with the attenuation correction data,
wherein detecting the motion comprises:
calculating measurement between each pair of the plurality of MR scan data sets, and
comparing the respective calculated similarity measurements to identify a time period during which the motion occurred; and
wherein determining the attenuation correction data comprises:
selecting a pair of MR scan data sets of the plurality of MR scan data sets acquired outside of the identified time period; and
interpolating between the pair of MR scan data sets to determine the attenuation correction data.

13. The data processing system of claim 12, wherein the processor is further configured to calculate a similarity measurement for each MR scan data set of the plurality of MR scan data sets.

* * * * *